United States Patent [19]
Pirotzky et al.

[11] Patent Number: 5,977,340
[45] Date of Patent: Nov. 2, 1999

[54] **ANTISENSE OLIGONUCLEOTIDES FOR INHIBITING *HELICOBACTER PYLORI* ACTIVITY**

[75] Inventors: Eduardo Pirotzky, Paris; Soudhir Colote, Les Ulïs, both of France

[73] Assignee: Societe de Conseils de Recherches et d'Applications Scientifiques (S.C.R.A.S.), France

[21] Appl. No.: 08/930,371

[22] PCT Filed: Mar. 18, 1996

[86] PCT No.: PCT/FR96/00407

§ 371 Date: Oct. 1, 1997

§ 102(e) Date: Oct. 1, 1997

[87] PCT Pub. No.: WO96/29399

PCT Pub. Date: Sep. 26, 1996

[30] Foreign Application Priority Data

Mar. 17, 1995 [GB] United Kingdom .................... 9505438

[51] Int. Cl.⁶ ............................ C07H 21/02; C07H 21/04
[52] U.S. Cl. ...................... 536/24.5; 536/23.1; 536/24.1; 536/24.3; 536/24.31
[58] Field of Search ................. 536/231, 24.5, 536/24.1, 24.3, 24.32; 514/44; 435/375, 377

[56] References Cited

U.S. PATENT DOCUMENTS 5,527,678  6/1996  Blaser et al. ................................ 435/6

FOREIGN PATENT DOCUMENTS 9318150  9/1993  WIPO.

OTHER PUBLICATIONS

Uhlmann et al. "Antisense Oligonucleotides: A New Therapeutic Principle" Chemical Reviews. vol. 90(4): 543–584, Jun. 1990.
Agrawal, S. "Antisense Oligonucleotides: Towards Clinical Trials" TIBTECH vol. 14:376–387, Oct. 1996.
Branch, D. "A Good Antisense is Hard to Find" TIBS vol. 23:45–50, Feb. 1998.
Telford et al, "Unravelling . . and Vaccines", Trends in Biotechnology vol. 12, No. 10, Oct. 1, 1994, pp. 420–456.
G. Zon, "Oligonucleotide . . . Agents", Pharmaceutical Reseach, vol. 5 (1988), pp. 539–549.
Phadnis et al, "pathological . . . *Helicobacter pylori*", Infection and Immunity, vol. 62, No. 5, 1994 pp. 1557–1565.
Tummuru et al, "Infection and Immunity", vol. 61, No. 5, (1993), pp. 1799–1809.

*Primary Examiner*—Nancy Degen
*Assistant Examiner*—Sean M. Garry
*Attorney, Agent, or Firm*—Bierman, Muserlian and Lucas

[57] ABSTRACT

Antisense oligonucleotides that selectively hybridise with one or more genes necessary for *Helicobacter pylori* (H. pylori) activity, and particularly with the CagA cytotoxicity-associated immunodominant antigen, flagellin (flaA and flaB) or vacuolating cytotoxin (vacA), are disclosed. Pharmaceutical compositions containing said antisense oligonucleotides, and the use thereof for treating atrophic gastritis, peptic and duodenal ulcers, gastric atrophy or stomach cancer, are also disclosed.

12 Claims, No Drawings

ANTISENSE OLIGONUCLEOTIDES FOR INHIBITING *HELICOBACTER PYLORI* ACTIVITY

The present invention concerns antisense oligonucleotides which selectively hybridize with one or more genes necessary for the action of *Helicobacter pylori* (H. pylori), pharmaceutical compounds comprising them and their use as *Helicobacter pylori* inhibitors.

*Helicobacter pylori* (H. pylori) is a microaerophilic bacterium, gram negative, colonizing the intercellular interstices and junctions of the human gastric mucous membrane and establishing a chronic infection with numerous different clinical manifestations such as atrophic gastritis, peptic and duodenal ulcer, gastric atrophy, and gastric carcinoma. The numerous clinical isolated substances have permitted classification of H. pylori into two groups based on the presence or the absence of vacuolizing cytotoxin. In vitro experiments have shown that the virulent nature of the bacterium may be connected to its mobility and to the presence of vacuolizing cytotoxin. Likewise, there is a direct relationship between the expression of cytotoxin and the presence of an immunodominant CagA antigen exposed on the surface. Thus, inhibition of the mobility of the bacterium and/or expression of the cytotoxic factor may prevent the manifestation of clinical symptoms. One of the ways to inhibit these factors comprises using antisense oligonucleotides to block the expression of the coding of the genes for the immunodominant antigen associated with the CagA cytotoxicity and/or flagellin (flaA and flaB) and/or the vacuolizing cytotoxin (vacA).

The antisense strategy is a therapeutic approach whose purpose is the selective modulation of the expression of the genes by a highly selective association of a chain of nucleotides (oligonucleotides) with its supplementary sequence on RNA or DNA and consequently the inhibition of the synthesis of the corresponding protein.

The oligonucleotides complementary to the products of transcription are called "antisense" oligonucleotides. Nucleotides having the same sequence as the products of transcription are called "sense" oligonucleotides. Initially, these compounds were logically intended to inhibit the formation of a product of the gene by suppression of the corresponding messenger RNA via the hydrolysis mechanism catalyzed by RNAse H. It soon turned out that the mechanism of action of these antisense oligonucleotides was not so simple. These oligonucleotides may interact with a certain number of cell targets not containing nucleic acid. These oligonucleotides may interact with the gene to form triple helix structures and inhibit the formation of products of transcription. Oligonucleotides may interact with the intron-exon junctions of pre-messenger RNA, thus interfering with the correct splicing of the product of transcription. Oligonucleotides may hybridize with messenger RNA in the cytoplasm forming an RNA-DNA complex which is quickly degraded by the RNAas H enzyme or by impeding the ribosome complex from splicing onto the messenger RNA and thus blocking the translation. Oligonucleotides, and more especially modified oligonucleotides, may interact with a number of cellular products such as proteins. These interactions may be sequence specific (for example: transcription factors) or non-sequence specific (for example: growth factors).

Oligonucleotides are very often used as a probe, for example for the detection or isolation of a polynucleotide and/or as a primer for the transcription and/or replication of target sequences (N. A. Innis et al., PCR Protocols: A Guide to Methods and Applications, 1990, Academic Press, Inc., San Diego, Calif.). Thus it is that oligonucleotides have been used during studies on *Helicobacter pylori* (WO-A-93/18150) and more especially on vacuolizing cytotoxin vacA (S. Phadnis et al, Infection and Immunity, vol. 62, No. 5, 1994, pp. 1557–1565) or the CagA antigen (M. Tummuru et al., Infection and Immunity, vol. 61, Nos. 5, 3, Washington, DC, pp. 1799–1809, and A. Covacci et al., Proceedings of the National Academy of Sciences of the USA, vol. 90, No. 12, 1993, Washington, DC, pp. 5791–5795) via the PCR (polymerase chain reaction). These oligonucleotides have never been used for therapeutic purposes in the domain of *Helicobacter pylori;* moreover, the determination of the antibacterial power has never been suggested.

The invention concerns antisense oligonucleotides which selectively hybridize with one or more genes necessary to the action of *Helicobacter pylori* in order to inhibit the role of *Helicobacter pylori*.

The invention concerns more especially antisense oligonucleotides which hybridize selectively with the coding of the genes for the immuno-dominant antigen associated with CagA cytotoxicity and/or flagellin (flaA and flaB) and/or vacuolizing cytotoxin (vacA). Oligonucleotides preferably contain 8 to 35 units. Most preferably, the oligonucleotide contains 10 to 25 units.

The term "oligonucleotide" represents an oligonucleotide composed of bases, of phosphodiester bonds and of sugars well known by specialists in the field. The term oligonucleotides likewise includes oligonucleotides whose sequence has been modified either all along the length of the oligonucleotide or in the 5' position and/or in the 3' position. In fact, oligonucleotides are sensitive to enzymes, the nucleases which break them down into nucleotides; oligonucleotides become resistant to nucleases by modification for example of the chemical nature of the sugar itself or phosphate—sugar linkage. Thus, phosphodiester linking may be replaced for example by a phosphorothioate, phosphorodithioate, methyl phosphonate, phosphoramidate, phosphoethyl triester, butyl amidate, piperazidate, or morpholidate linkage. Other types of modifications may be furnished all along the length of the oligonucleotide or at its 5' and/or 3' ends to render the oligonucleotides more resistant to a biological environment. The phosphate bonds between the nucleotides may also be replaced by amide bonds (peptide nucleic acids). Moreover, the transmembrane passage of the oligonucleotide may be favored by rendering the latter more hydrophobic: this may be achieved for example by attaching hydrophobic substitutes such as cholesterol or aromatic rings, or a polymer. Modified bases may be incorporated partially or along the whole length of the oligonucleotide. Conformationally modified nucleotides resistant to nucleases or with improved properties of intracellular absorption or hybridization may be incorporated partially or all along the length of the oligonucleotide. Thus, the expression "oligonucleotide" likewise represents a nucleotide whose skeleton is modified according to any of the methods described above or by any other method well known to the specialist in the field.

More especially, the subject matter of the invention are oligonucleotides of sequences SEQ ID No. 1 through SEQ ID No. 24 respectively. Oligonucleotides of sequences SEQ ID No. 13–24 are oligonucleotides in which all of the phosphodiester bonds have been modified to phosphorothioate. Their complementary sequences or the sense oligonucleotides according to the invention may also be used.

The invention likewise concerns antisense oligonucleotides containing at least one fragment of one of the sequences selected from among the sequences SEQ ID No. 1 through SEQ ID No. 24.

The oligonucleotides of the invention may be synthesized by any of the known methods of chemical oligonucleotide synthesis. Antisense oligonucleotides are very advantageously prepared by using any automatic synthesizer of nucleic acid available on the market. One of these methods of synthesizing oligonucleotides is the beta-cyanoethyl phosphoramidate method described by S. L. Beaucage et al. (Tet. Let. 22 [1981], 1859–1862).

The invention likewise has as its object pharmaceutical compounds comprising as the active principle at least one antisense oligonucleotide according to the invention, mixed with a pharmaceutically acceptable vehicle and/or excipient, according to the mode of administration chosen. The compound may be administered by means of topical, systemic, or local treatment. It may assume the form of a liquid for injection, liposome, time release formula, or in the form of a gel, of an unguent for local application, or in any other acceptable form according to the mode of administration chosen.

Finally, the invention concerns the use of oligonucleotides according to the invention for the preparation of medications to inhibit the role of *Helicobacter pylori*. The invention more especially concerns the use of oligonucleotides according to the invention for the preparation of medications for the treatment of atrophic gastr[itis], peptic or duodenal ulcer, gastric atrophy, or gastric carcinoma.

The inhibitor role of oligonucleotides is determined by a study of the antibacterial strength using stocks of *Helicobacter pylori*.

Thus, this study includes on the one hand a study of the bacteriostatic strength in an agar-agar medium containing oligonucleotides. Bacteriostasis is defined by that concentration of oligonucleotides which does not allow any or more than 5 colonies of *Helicobacter pylori* to survive after 3 days of incubation at 37 degrees C in a microaerophilic atmosphere.

It includes on the other hand a study of bactericidal strength by replication using the "velvet technique."

The stocks tested are the following: a typical reference stock of *Helicobacter pylori* (CIP 10-3995) sensitive to Metronidazol, and a C stock resistant to Metronidazol.

The culture medium used is Colombia agar-agar with 10% horse blood added, freshly prepared.

Study of bacteriostatic strength:

Each oligonucleotide is incorporated into the medium kept supercooled at 45 degrees C so as to obtain final concentrations of the agar-agars of 1, 10, and 20 micromoles. The agar-agars are cooled in sterile Petri dishes 45 mm in diameter under a volume of 10 ml.

After solidification, the agar-agars are dried for 18 hours at ambient temperature.

The stocks of *Helicobacter pylori* are put into suspension in Brucella medium and the concentration is adjusted to level 3 on the MacFarland scale.

The dishes are immediately placed in an oven at 37 degrees C in a microaerophile atmosphere (Generbag-BioMerieux System).

The reading is done after 3 days of incubation.

Study of bactericidal strength:

Each dish showing bacteriostasis is replicated with a disk of sterile velvet on a box of agar-agar without oligonucleotide.

After 3 days of incubation at 37 degrees C in a microaerophile atmosphere the bactericide is examined for the absence of a subculture.

Thus, with the oligonucleotides SEQ ID No. 15, SEQ ID No. 16, SEQ ID No. 19, SEQ ID No. 20, SEQ ID No. 21, and SEQ ID No. 22, at a concentration of 20 micromoles, there is observed a clear reduction in the bacterial growth of the two stocks tested.

We claim:

1. An antisense oligonucleotide comprising 15 to 25 units which hybridizes selectively with the genes for the immunodominant antigen associated with CagA cytotoxicity and/or flagellin (flaA and flaB) and/or vaculizing cytotoxin (vacA) and said oligonucleotide is one of SEQ ID Nos: 1 to 24 or contains therein one of SEQ ID Nos: 1 to 24.

2. An oligonucleotide according to claim 1 whose sequence is selected from the sequences SEQ ID No: 1 through SEQ ID No: 12.

3. An oligonucleotide according to claim 1 whose backbone is modified.

4. An oligonucleotide according to claim 3 in which a nucleotide base is modified.

5. An oligonucleotide according to claim 4 in which the modified nucleotide base has the alpha-anomer conformation.

6. An oligonucleotide according to claim 3 in which at least one of the phosphodiester bonds is modified.

7. An oligonucleotide according to claim 6 in which at least one of the phosphodiester bonds is modified to phosphorothioate.

8. An oligonucleotide according to claim 7 whose sequence is selected from among the sequences SEQ ID No: 13 through SEQ ID No: 24.

9. An oligonucleotide according to claim 3 in which either position 5' or position 3' or positions 5' and 3' are modified.

10. An oligonucleotide according to claim 9 in which either position 5' or position 3' or positions 5' and 3' are modified by the substitution of a hydrophobic group.

11. An oligonucleotide according to claim 9 in which either position 5' or position 3' or positions 5' and 3' are modified by the substitution of a protector group.

12. An antisense oligonucleotide consisting of 15 to 25 units wherein said antisense oligonucleotide comprises any one of SEQ ID Nos: 1–24.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (iv) ANTI-SENSE: YES (xi) SEQUENCE DESCRIPTION: SEQ ID NO: 1:

TTCGTTAGTC ATTGT                                                          15

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (iv) ANTI-SENSE: YES (xi) SEQUENCE DESCRIPTION: SEQ ID NO:2:

AGCGACAGCG TTATC                                                          15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:3:

CGTTGCAGGC GTCTA                                                          15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:4:

GTATCTACAA CCAAT                                                          15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:5:

TGACTAATGC TCCTA                                                          15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:6:

AGCGCCTGTA GCGAT                                                          15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:7:

TTTGTATTGA CCTGA                                                          15

(2) INFORMATION FOR SEQ ID NO:8:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO:8:

ATCTCTCCAA TGAAG                                                               15

(2) INFORMATION FOR SEQ ID NO:9:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO:9:

TTGGAACTAT TATCG                                                               15

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO:10:

TGTTCCAACT CTTTG                                                               15

(2) INFORMATION FOR SEQ ID NO:11:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO:11:

CTACCGCATG AGAAG                                                               15

(2) INFORMATION FOR SEQ ID NO:12:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (iv) ANTI-SENSE: YES (xi) SEQUENCE DESCRIPTION: SEQ ID NO:12:

CCTAAGCCCT GAGCT                                                               15

(2) INFORMATION FOR SEQ ID NO:13:

(i) SEQUENCE CHARACTERISTICS:
            (A) LENGTH: 15 base pairs
            (B) TYPE: nucleic acid
            (C) STRANDEDNESS: single

```
            (D) TOPOLOGY:  linear (iv) ANTI-SENSE: YES (ix) FEATURE:
            (A) NAME/KEY:  modified-bond
            (B) LOCATION:  1-15
            (C) OTHER INFORMATION:/note ="Phosphorothioate
                bond"

(xi) SEQUENCE DESCRIPTION:  SEQ  ID NO:13:

TTCGTTAGTC ATTGT                                                                   15

(2) INFORMATION FOR SEQ ID NO:14:

(i) SEQUENCE CHARACTERISTICS:
            (A) LENGTH:  15 base pairs
            (B) TYPE:  nucleic acid
            (C) STRANDEDNESS:  single
            (D) TOPOLOGY:  linear (iv) ANTI-SENSE: YES (ix) FEATURE:
            (A) NAME/KEY:  modified-bond
            (B) LOCATION:  1-15
            (C) OTHER INFORMATION:/note ="Phosphorothioate
                bond"

(xi) SEQUENCE DESCRIPTION:  SEQ  ID NO:14:

AGCGACAGCG TTATC                                                                   15

(2) INFORMATION FOR SEQ ID NO:15:

(i) SEQUENCE CHARACTERISTICS:
            (A) LENGTH:  15 base pairs
            (B) TYPE:  nucleic acid
            (C) STRANDEDNESS:  single
            (D) TOPOLOGY:  linear (iv) ANTI-SENSE: YES (ix) FEATURE:
            (A) NAME/KEY:  modified-bond
            (B) LOCATION:  1-15
            (C) OTHER INFORMATION:/note ="Phosphorothioate
                bond"

(xi) SEQUENCE DESCRIPTION:  SEQ  ID NO:15:

CGTTGCAGGC GTCTA                                                                   15

(2) INFORMATION FOR SEQ ID NO:16:

(i) SEQUENCE CHARACTERISTICS:
            (A) LENGTH:  15 base pairs
            (B) TYPE:  nucleic acid
            (C) STRANDEDNESS:  single
            (D) TOPOLOGY:  linear (iv) ANTI-SENSE: YES (ix) FEATURE:
            (A) NAME/KEY:  modified-bond
            (B) LOCATION:  1-15
            (C) OTHER INFORMATION:/note ="Phosphorothioate
                bond"

(xi) SEQUENCE DESCRIPTION:  SEQ  ID NO:16:

GTATCTACAA CCAAT                                                                   15

(2) INFORMATION FOR SEQ ID NO:17:
```

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:17:

TGACTAATGC TCCTA                                                          15

(2) INFORMATION FOR SEQ ID NO:18:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:18:

AGCGCCTGTA GCGAT                                                          15

(2) INFORMATION FOR SEQ ID NO:19:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:19:

TTTGTATTGA CCTGA                                                          15

(2) INFORMATION FOR SEQ ID NO:20:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:20:

ATCTCTCCAA TGAAG                                                          15

(2) INFORMATION FOR SEQ ID NO:21:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:21:

TTGGAACTAT TATCG                                      15

(2) INFORMATION FOR SEQ ID NO:22:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:22:

TGTTCCAACT CTTTG                                      15

(2) INFORMATION FOR SEQ ID NO:23:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION:  SEQ  ID NO:23:

CTACCGCATG AGAAG                                      15

(2) INFORMATION FOR SEQ ID NO:24:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (iv) ANTI-SENSE: YES (ix) FEATURE:
        (A) NAME/KEY:  modified-bond
        (B) LOCATION:  1-15
        (C) OTHER INFORMATION:/note ="Phosphorothioate
            bond"

(xi) SEQUENCE DESCRIPTION: SEQ ID NO:24:

CCTAAGCCCT GAGCT                                              15